(12) United States Patent  (10) Patent No.: US 8,581,008 B2
Kaizik et al.  (45) Date of Patent: Nov. 12, 2013

(54) PROCESS FOR PREPARING
α,β-UNSATURATED $C_{10}$-ALDEHYDES

(75) Inventors: Alfred Kaizik, Marl (DE); Dirk Fridag, Haltern am See (DE); Hans-Gerd Lueken, Marl (DE); Wilfried Bueschken, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 11 days.

(21) Appl. No.: 13/256,116

(22) PCT Filed: Feb. 23, 2010

(86) PCT No.: PCT/EP2010/052271
§ 371 (c)(1),
(2), (4) Date: Sep. 27, 2011

(87) PCT Pub. No.: WO2010/105892
PCT Pub. Date: Sep. 23, 2010

(65) Prior Publication Data
US 2012/0123169 A1  May 17, 2012

(30) Foreign Application Priority Data
Mar. 17, 2009 (DE) .......................... 10 2009 001 594

(51) Int. Cl.
*C07C 45/45* (2006.01)
(52) U.S. Cl.
USPC ........................................ 568/461; 568/463
(58) Field of Classification Search
USPC ........................................ 568/461, 463, 464
See application file for complete search history.

(56) References Cited

U.S. PATENT DOCUMENTS

| | | |
|---|---|---|
| 6,340,778 B1 | 1/2002 | Bueschken et al. |
| 6,433,230 B1 | 8/2002 | Bueschken et al. |
| 6,680,414 B2 | 1/2004 | Knoop et al. |
| 7,138,552 B2 | 11/2006 | Kaizik et al. |
| 7,381,838 B2 | 6/2008 | Wiese et al. |
| 7,524,997 B2 | 4/2009 | Kaizik et al. |
| 2006/0161017 A1 | 7/2006 | Grass et al. |
| 2010/0249464 A1 | 9/2010 | Lueken et al. |
| 2011/0060169 A1 | 3/2011 | Kaizik et al. |
| 2011/0130595 A1 | 6/2011 | Lueken et al. |

FOREIGN PATENT DOCUMENTS

| | | |
|---|---|---|
| EP | 1 103 538 | 5/2001 |
| EP | 1 106 596 | 6/2001 |

OTHER PUBLICATIONS

U.S. Appl. No. 13/502,226, filed Apr. 16, 2012, Kaizik, et al.
International Search Report issued Apr. 23, 2010 in PCT/EP10/052271filed Feb. 23, 2010.
U.S. Appl. No. 13/386,523, filed Jan. 23, 2012, Grass, et al.
U.S. Appl. No. 13/498,690, filed Mar. 28, 2012, Kaizik, et al.
U.S. Appl. No. 13/703,925, filed Dec. 13, 2013, Franke, et al.
U.S. Appl. No. 13/822,650, filed Mar. 13, 2013, Franke, et al.
U.S. Appl. No. 13/988,431, filed May 20, 2013, Nordhoff, et al.
U.S. Appl. No. 13/883,808, filed May 7, 2013, Franke et al.

*Primary Examiner* — Sikarl Witherspoon
(74) *Attorney, Agent, or Firm* — Oblon, Spivak, McClelland, Maier & Neustadt, L.L.P.

(57) ABSTRACT

The invention relates to a method for continuously producing α,β-unsaturated $C_{10}$-aldehydes from aliphatic $C_5$-aldehydes, comprising the following steps: aldol-condensing aliphatic $C_5$-aldehydes into α,β-unsaturated $C_{10}$-aldehydes in the presence of an aqueous base in a tube reactor; phase separating the output of the tube reactor into an aqueous catalyst phase and an organic product phase; separating the organic product phase into α,β-unsaturated $C_{10}$-aldehydes, aliphatic $C_5$-aldehydes, and auxiliary products; discharging a part of the aqueous catalyst phase to remove the reaction water and supplementing said part with liquor solution and subsequently returning said part to the tube reactor. The task of the invention is to improve a method of said kind in a way such that it requires lower energy input. This is achieved in that the aliphatic $C_5$-aldehydes and/or the α,β-unsaturated $C_{10}$-aldehydes are dispersed in the aqueous base as drops, wherein the average Sauter diameter of the drops is between 0.2 mm and 2 mm.

18 Claims, 2 Drawing Sheets

PROCESS FOR PREPARING α,β-UNSATURATED $C_{10}$-ALDEHYDES

Figure 1:
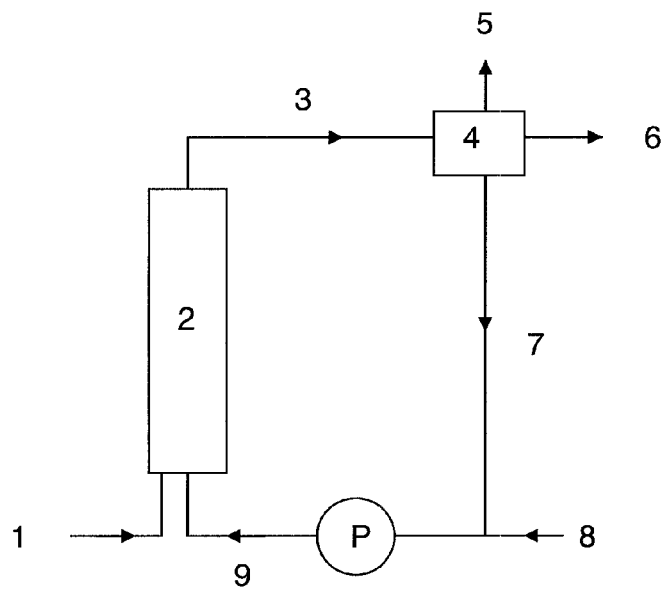

The present invention relates to the preparation of α,β-unsaturated $C_{10}$-aldehydes, especially 2-propylhept-2-enal, by aldol condensation of $C_5$-aldehydes, especially n-pentanal, with the aid of a continuous process according to the preamble of claim 1.

A process of this type is known from DE 199 57 522.

Total hydrogenation of α,β-unsaturated $C_{10}$-aldehydes affords decanols, which are sought-after plasticizer alcohols. Decenols are intermediates for the preparation of decanoic acids, which can be used to produce peresters, detergents, plasticizers and lubricants.

DE 101 08 474, DE 101 08 475, DE 101 08 476 and DE 102 25 282 mention, among other things, that $C_5$-aldehydes, especially n-pentanal, can be converted to α,β-unsaturated $C_{10}$-aldehydes. Exact conditions for performance of the aldol condensation are not disclosed. It is merely pointed out that α,β-unsaturated $C_{10}$-aldehydes can be prepared from aliphatic $C_5$-aldehydes in an analogous manner to octenal and 2-ethylhex-2-enal from n-butanal (butyraldehyde).

In the practised art, preferably basic homogeneous catalysts in the form of bases, especially in the form of aqueous NaOH, are used in the conversion of aliphatic $C_5$-aldehydes to α,β-unsaturated $C_{10}$-aldehydes by aldol condensation. A first reaction step of the aldolization forms a $C_{10}$-hydroxyaldehyde ($C_{10}$-aldol), from which a second reaction step forms the unsaturated $C_{10}$-aldehyde (decenal) by elimination of water. The reaction proceeds with involvement of two phases (organic aldehyde phase, aqueous catalyst phase), which are virtually immiscible. The achievement of high conversions and selectivities therefore requires that the two mutually immiscible liquid phases are intimately contacted with one another during the reaction in order to overcome the inhibition of mass transfer between the phases. Suitable process technology measures therefore have to generate a maximum mass transfer area between the two phases.

According to the prior art, mass transfer between the organic pentanal-containing phase and the aqueous catalyst phase is achieved by intensive stirring when stirred tanks are used, and by turbulent flow when tubular reactors are used.

WO 93/20034 describes the aldol condensation of aliphatic $C_5$-aldehydes to α,β-unsaturated $C_{10}$-aldehydes in a stirred tank. The catalyst used is approx. 2% sodium hydroxide solution at a reaction temperature of 120° C. The reaction is performed continuously in a stirred tank at a phase ratio of organic phase to sodium hydroxide solution in the range from 0.5:1 to 5:1. In order to achieve a conversion of 97% in straight pass, a residence time of 50 minutes is required. Preferably, the aim is a conversion of approx. 70% at a residence time of 30 minutes. The unconverted $C_5$-aldehydes are removed by distillation from the reaction product and recycled into the reactor.

In DE 199 57 522, aliphatic $C_5$-aldehydes are converted to α,β-unsaturated $C_{10}$-aldehydes in the presence of sodium hydroxide solution in a tubular reactor in which the organic phase is dispersed in the sodium hydroxide solution and which, according to examples, is operated with a loading factor greater than 9.92. The loading factor B is defined as follows:

$$B = PD/PS$$

PD [Pa/m] is a pressure drop based on length over the reactor under operating conditions and PS [Pa/m] an operand with the unit of a pressure based on length, defined as the ratio of mass flow M [kg/s] of all components in the reactor to the volume flow V [m³/s] of all components under operating conditions, multiplied by g=9.81 m/s².

This process can achieve pentanal conversions of more than 96% in high space-time yields at a sodium hydroxide solution/reactant ratio of approx. 100 to 1.

The processes according to WO 93/20034 and DE 199 57 522 have the disadvantage that a very high energy expenditure is needed for the performance thereof. This is caused in the stirred tank reaction in WO 93/20034 by the drive power of the stirrer units, and in the tubular reaction known from DE 199 57 522 by the flow losses resulting from the turbulences.

It is therefore an object of the present invention to develop a process of the type specified at the outset in such a way that the performance thereof requires less energy input at high product yields.

This object is achieved by dispersing the aliphatic $C_5$-aldehydes and/or the α,β-unsaturated $C_{10}$-aldehydes as droplets in the aqueous base, the average Sauter diameter of the droplets being in the range from 0.2 mm to 2 mm.

The invention therefore provides a process for continuously preparing α,β-unsaturated $C_{10}$-aldehydes from aliphatic $C_5$-aldehydes, which comprises the following steps:

a) aldol condensation of aliphatic $C_5$-aldehydes to give α,β-unsaturated $C_{10}$-aldehydes in the presence of an aqueous base in a tubular reactor;
b) phase separation of the output from the tubular reactor into an aqueous catalyst phase and an organic product phase;
c) separation of the organic product phase into α,β-unsaturated $C_{10}$-aldehydes, aliphatic $C_5$-aldehydes and by-products;
d) discharge of a portion of the aqueous catalyst phase to remove the water of reaction and supplementation with fresh base and subsequent recycling into the tubular reactor;

wherein the aliphatic $C_5$-aldehydes and/or the α,β-unsaturated $C_{10}$-aldehydes are dispersed as droplets in the aqueous base; and wherein the average Sauter diameter of the droplets is in the range from 0.2 mm to 2 mm.

One of the fundamental findings on which the invention is based is that a mass transfer between the phases of the reaction is particularly effective when the reactant or the reactant/product mixture is dispersed in the aqueous base while maintaining the droplet size specified. It was found that, surprisingly, this droplet size can be established with mixing modules with a very low energy input, and additionally ensures high mass transfer and therefore a high product yield.

Mixing modules in the context of the invention are passive internals in the flow path, which accomplish the inventive dispersion.

The inventive effect can be explained or interpreted as follows:

The aldol condensation of aliphatic $C_5$-aldehydes, being a biphasic reaction, is determined crucially by the phase interface between the disperse and continuous phases. The organic $C_5$-aldehyde phase is the disperse phase, the aqueous NaOH the continuous phase. The size of the phase interface depends on the droplet diameter and the proportion of the disperse phase φ. For the specific phase interface a:

$$a = 6 * \phi / d_s \; [1/m]$$

where $d_s$ is the Sauter diameter summed over all droplets.

The Sauter diameter $d_s$ describes the mean droplet diameter of the disperse $C_5$-aldehyde phase. The finer the droplet distribution (the smaller the Sauter diameter), the greater the exchange area.

The calculation of the specific phase interface requires the Sauter diameter, which has to be determined using in-house experimental results or those from the literature [Coulaloglou C. A. AICHE Journal, 22, No. 2 (1976), pp. 289-295, 10 and R. K. Thakur et al. Trans IChemE, Vol 81, 2003, pp. 787-826].

For stirred liquid/liquid systems, several authors, with reference to experiments, have produced a series of calculation equations for the determination of the Sauter diameter. The majority of the equations known from the literature can be summarized by the following equation:

$$d_S/d_R = C_1 * We^{-0.6}(1+C_2*\phi)$$

In this equation, $C_1$ and $C_2$ are system-dependent constants which are in the range from 0.027 to 0.081 for $C_1$ and in the range from 0.97 to 23.3 for $C_2$. We is the Weber number and $d_R$ is the diameter of the stirrer. The We number is the ratio of dispersing power and interfacial power.

$$We = (1/\sigma)*\rho*d_R^3*n^2$$

In this equation, n is the stirrer speed, $\rho$ is the density and $\sigma$ is the surface tension.

To calculate the mean droplet diameter when using stirred tanks with an installed stirrer, the following equation can be used:

$$d_S = d_R * We^{-0.6}(1+4.47*\phi)*0.081$$

Similar correlations are also known to any person skilled in the art from the literature for the dispersion of liquid/liquid systems in the case of use of static mixers, for example Sulzer or Kenicks mixers.

For the dispersion of low-viscosity liquids, for example, static mixers of the SMV type from Sulzer are recommended.

For the static SMV mixers, the mean Sauter droplet diameter $d_S$ can be determined by the following relationship (Streiff F.; Recent Prog. Genie Proc. 11. No. 51 (1997) p. 307):

$$d_S/d_h = 0.21 * We^{-0.5} Re^{0.15}$$

where $d_h$ is the hydraulic diameter of the mixing element channels.

The Weber number and the Reynolds number are defined as follows:

$$We = \rho * d_h * u^2 / (\sigma * \epsilon^2)$$

and $$Re = \rho * d_h * u / (\eta * \epsilon)$$

where u is the superficial velocity of liquid phase (m/s), $\epsilon$ is the relative void volume of the mixer and $\eta$ is the dynamic viscosity (Pa*s) of the continuous phase.

The pressure drop in a flow tube with a static mixer can be calculated approximately for multiphase flow of liquids in the same way as for single-phase flow:

$$\Delta p = \xi * \rho * L * u^2 / (2 * d_h)$$

where $\xi$ is the geometry-dependent resistance coefficient. A list of the resistance coefficients for static mixers of different geometry can be found in the technical literature (R. K. Thakur et al. Trans IChemE, Vol 81, 2003, pp. 787-826).

With knowledge of the pressure based on length PD (PD=$\Delta$p/L) and the PS operand, it is possible, as disclosed in DE 199 57 522, to calculate the load parameter B.

A common feature of the static mixers is that their hydrodynamic behaviour has been studied in detail and is therefore known. This fact can be considered as a key for the reliable scaleup of experimental results to the industrial scale. The scaleup risk for static mixers is very low owing to the strictly defined geometry and flow regime. As a basis for the model application, two prerequisites are indispensible: equal substance values and equal geometric similarity. The application criterion requires an equal energy input based on volume and an identical flow state. The energy input in the case of use of static mixers can be calculated according to F. Streiff (Recents Progres en Genie des Procedes 11. No. 51, 1997), according to the following equation:

$$E_d = (\Delta p * V)/(V_m * \rho) = (Ne*u^3)/(d_R*\epsilon)$$

where $V_m$ is the mixer volume in m$^3$, V is the volume flow in m$^3$/s and $d_R$ is the tube diameter. Ne is the Newton number, a modified resistance number which is likewise used by Sulzer for calculation of the pressure drop. The Ne numbers for the individual mixer types are known and catalogued in tabular form.

For the estimation of the energy input of the stirrer, its power P is first calculated from the known relationship (power equation):

$$P = Ne * \rho * n^3 * d_R^5$$

where Ne is the Newton number of the stirrer. It depends on the Re number. The Ne number can be inferred from the Ne—Re diagrams for different stirrer systems. Such diagrams can be found in the technical literature in several references, for example in "Rührtechnik—Theorie and Praxis" [Stirring technology—Theory and practice], Springer Verlag, 1999 by M. Zlokarnik. When the stirrer output and the reaction volume $V_R$ are known, it is possible to calculate the volume-based energy input from the quotient P to $V_R$.

However, the abovementioned equations alone cannot calculate the yield and the selectivity of the $\alpha,\beta$-unsaturated $C_{10}$-aldehydes. There is a lack of further influencing parameters, for example temperature, phase ratio, residence time or base composition, which are just as important.

With regard to this, the invention teaches the following:

It has been found that aliphatic $C_5$-aldehydes are converted to an extent of more than 96% to $\alpha,\beta$-unsaturated $C_{10}$-aldehydes when the reaction is performed in a tubular reactor which comprises at least one mixing module which disperses the $C_5$-aldehyde reactant into droplets with an average diameter (Sauter diameter) of 0.2 mm to 2 mm in the continuous catalyst phase (process liquor) which consists of sodium hydroxide solution and sodium salts of carboxylic acids and has a sodium content of 0.6 to 1.75% by mass and a pH in the range from 12.5 to 13.5.

Further advantageous embodiments of the invention are evident from the dependent claims and from the description which follows.

The advantages of the process according to the invention lie in the high product yield in straight pass and in low specific energy consumption, the energy consumption being determined by the pump output; the higher the pump output, the higher the pressure drop and, associated with this, the higher the specific energy input.

Feedstocks

In the process according to the invention, 3-methylbutanal, n-pentanal and mixtures thereof may be used. These mixtures may have up to 10% by mass, preferably less than 5% by mass, of 2-methylbutanal. A preferred reactant is n-pentanal which contains less than 10% by mass, especially less than 5% by mass, of 2-methylbutanal, and less than 3% by mass of 3-methylbutanal. Very particular preference is given to using a $C_5$-aldehyde mixture which has an n-pentanal content of at least 95%.

It should be pointed out, however, that it is also possible in the process according to the invention to use $C_5$-aldehyde mixtures which have a different composition from the abovementioned mixtures. For example, the feedstocks could comprise small amounts of pentanols.

An n-pentanal-rich $C_5$-aldehyde mixture can be obtained by hydroformylation of 1-butene, 2-butene or mixtures thereof, each of which have only small proportions of isobutene. A process for preparing n-pentanal from 2-butenes is described, for example, in DE 10 2008 002187.3.

To form the process liquor, sodium hydroxide solution is used in the process according to the invention. The sodium hydroxide solution forms the process liquor together with the return liquor. The return liquor comprises, as well as sodium hydroxide, sodium salts of carboxylic acids, principally of pentanoic acids. The carboxylic salts have been formed essentially by Cannizzaro reaction.

In the process according to the invention, the sodium content of the process liquor at the reactor inlet is 0.60 to 1.75% by mass, especially 1.1 to 1.20% by mass. To adjust the sodium concentration of the process liquor, sodium hydroxide solution is fed into the return liquor with a concentration greater than 2.5% by mass. In order to introduce little water into the reaction system, preference is given to using sodium hydroxide solution with a relatively high concentration. In the process according to the invention, preference is given to using sodium hydroxide solution in the concentration range from to 30% by mass, for example at 10% by mass.

Tubular Reactor with Static Mixers

The process according to the invention is performed in a tubular reactor which has at least one mixing module, preferably more than one mixing module. More particularly, the number of mixing modules is 1 to 30, very particularly 10 to 20.

A mixing module means a static mixer, i.e. a passive component which has no direct intrinsic energy requirement.

The tubular reactor consists of a tube which is preferably aligned vertically. The flow through it may be from bottom to top or vice versa. An industrial reactor may also consist of a plurality of tubes arranged in parallel, which are connected to one another by U-tubes.

A mixing module is preferably present at the reactor inlet. Voids are present between the mixing modules. The proportion by volume of the total volume of the reactor outside the mixing module(s) is 20 to 80%, especially 30 to 60%. The mixing modules may have equal or different distances from one another. The distance between the mixer modules preferably decreases in flow direction. The distances of the mixer modules from one another are, depending on the intended superficial velocity, the phase ratio between reactant and catalyst phases, the reaction progress and the mixer type, 0.2 to five times the mixing module length, especially 0.5 to two times the mixing module length.

The mixing module consists of a static mixer or of an arrangement of two or more, preferably two, static mixers.

When the mixer module consists of two identical static mixers, they are preferably arranged twisted about the longitudinal axis of the reactor, especially twisted by an angle of 45° up to 90°. Mixing elements are preferably arranged in the mixer module with a distance of two tube diameters.

A mixing module may also consist of static mixers of different design. It may be advantageous that, in the case of a mixer module consisting of two static mixers, the first has a lower hydraulic diameter than the second. In this case, the first static mixer produces very small droplets and the second static mixer, as a result of selection of a greater hydraulic diameter, prevents the coalescence of the cluster of droplets.

The hydraulic diameter of the mixing elements of the mixer modules preferably decreases with flow direction.

The mixer modules in the reactor may be the same or different, i.e. they may be of the same design or of different designs.

The mixing elements used may be all static mixers which, under the intended reaction conditions, are capable of dispersing the organic phase in the catalyst phase in droplets with an average Sauter diameter in the range from 0.2 to 2.0 mm.

The static mixers used in the process according to the invention may be mixing elements which are suitable for the dispersion of two immiscible low-viscosity liquids, as are commercially available.

Reaction Conditions

According to the invention, the aldol condensation of the aliphatic $C_5$-aldehydes is performed in the temperature range from 100 to 150° C., especially in the range from 110 to 140° C., very particularly in the range from 120 to 140° C.

The reaction can be performed isothermally, adiabatically or polytropically in the temperature ranges specified. For example, a temperature of 120° C. at the reactor inlet and a temperature of 140° C. at the reactor outlet may be present.

The reaction pressure in the reactor is at least sufficiently high that both the process liquor and the organic substances (reactant and products) are present as liquid phases. The pressure is in the range from 0.2 to 1.0 MPa, preferably in the range from 0.3 to 0.5 MPa.

In the process according to the invention, the ratio [kg/kg] of process liquor to reactant at the reactor inlet is in the range from 5 to 40, especially is in the range from 10 to 15.

The average superficial velocity of the mixture of reactant and process liquor (assuming equal flow rate of the two phases) in the industrial reactor is in the range from 0.5 to 4 m/s, especially in the range from 1 to 2.5 m/s.

The average residence time of the reaction mixture in the reactor is 40 to 360 s, especially 60 to 180 s.

In the process according to the invention, the droplets of the organic phase dispersed in the process liquor, after leaving a mixer module, have an average Sauter diameter of 0.2 to 2 mm, especially one of 0.6 to 1.3 mm.

The loading factor is in the range from 0.2 to 0.8.

Workup

The reaction output is cooled and the organic phase is separated from the liquor phase. In the process according to the invention, the phase separation is effected within the temperature range from 60 to 130° C., especially in the range from 70 to 120° C., very particularly within the range from 90 to 110° C. According to the temperature selected, the separation times are 3 to 10 minutes. At temperatures above 90° C., the separation time is less than 8 minutes. The separation time is defined as the time after which the organic product of value phase is clear and free of traces of heterogeneous water.

To remove the heavy, aqueous phase from the light, organic phase, separators which enable phase separation solely utilizing gravity can be used. These gravitational separators can also be designed with internals as a coalescence-promoting measure to increase the separating performance. The use of internals accelerates the coalescence and sedimentation process. The coalescence aids used may, for example, be plates, random packings, fabric packings or fibre bed separators. Gravitational separators can be designed as horizontal vessels or as vertical vessels.

Alternatively to gravitational separators, it is also possible to use separators according to the centrifuging principle for liquid-liquid separation. These separate the heavy phase by means of centrifugal forces in a rotating drum.

In order to remove the heavy, aqueous phase, preference is given to using gravitational separators in the process according to the invention, preferably gravitational separators, designed as horizontal vessels with internals.

A portion of the liquor phase removed is discharged to remove the water of reaction; the other portion is recycled into the reactor. With the discharge stream, a portion of the carboxylic acids formed as by-products (as sodium salts) and sodium hydroxide are also removed. This stream can be sent to a wastewater treatment plant. However, it is also possible to work up this stream and partly recycle it into the process, as described, for example, in DE 198 49 922 and DE 198 49 924.

When the organic phase, as well as the α,β-unsaturated $C_{10}$-aldehydes and small amounts of unconverted reactant, comprises other by-products such as carboxylic salts, sodium hydroxide and dissolved water, traces of base and a portion of the carboxylic salts can be removed by water scrubbing. The water extract obtained can be used to make up the fresh base (not shown in FIGS. 1 to 4).

When pure n-pentanal is used as the reactant, the organic product phase contains two decenals, specifically cis- and trans-2-propylhept-2-enal.

When the n-pentanal used contains 2-methylbutanal and/or 3-methylbutanal, the organic phase may contain up to eight further α,β-unsaturated $C_{10}$-aldehydes.

The organic phase can be worked up by distillation. Some $C_5$ compounds removed can be recycled into the reactor.

The α,β-unsaturated $C_{10}$-aldehydes can be used to prepare decanoic acids (by selective hydrogenation and oxidation) or to prepare decanols (total hydrogenation).

In the case of preparation of decanols, it is optionally also possible to hydrogenate the crude mixture and to separate by distillation after the hydrogenation.

A further option in the present invention is to subject the reaction mixture, after leaving the reactor and before the phase separation, to a brief distillation. This involves decompressing the hot reaction mixture into a vessel. The distillate obtained is a mixture of water and principally $C_5$ compounds, which can be completely or partially recycled into the reactor. (Separation of the distillate and recycling of a portion of the organic distillate not shown in FIGS. 3 and 4.) Such a process is described, for example, in DE 199 56 410.

Process Variants

With reference to FIGS. 1 to 4, the present invention is described in detail hereinafter.

A block diagram of an embodiment in which the process according to the invention can be performed is shown in FIG. 1. The pentanal starting stream (1) is introduced into the tubular reactor (2) with the static mixers. The reaction mixture (3) leaving the reactor is separated in the separating vessel (4) into an organic phase (5) comprising the target product and a liquor phase, from which one portion (6) is discharged and the other portion (7) is recycled into the reactor (2) as stream (9) together with fresh base (8).

In FIG. 1, the pentanal starting stream (1), downstream of the circulation pump (P), can optionally be combined with stream (9) and introduced into the reactor.

Figure 2:
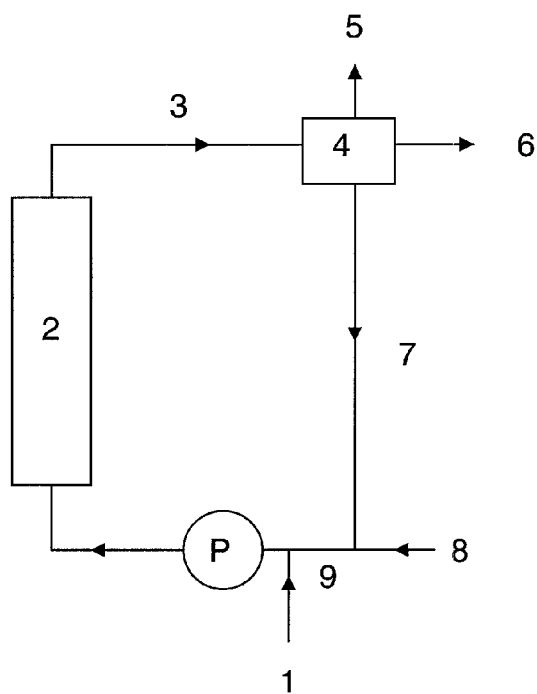

FIG. 2 shows a further embodiment of the process according to the invention. The process variant according to FIG. 2 differs from the variant according to FIG. 1 in that the pentanal starting stream (1) is introduced into the plant upstream of the circulation pump. As a result of the intensive mixing of the two phases, partial conversion already takes place in the circulation pump, such that the residence time in the reactor can be shortened. This effect is pronounced particularly in the case of centrifugal pumps.

Figure 3:
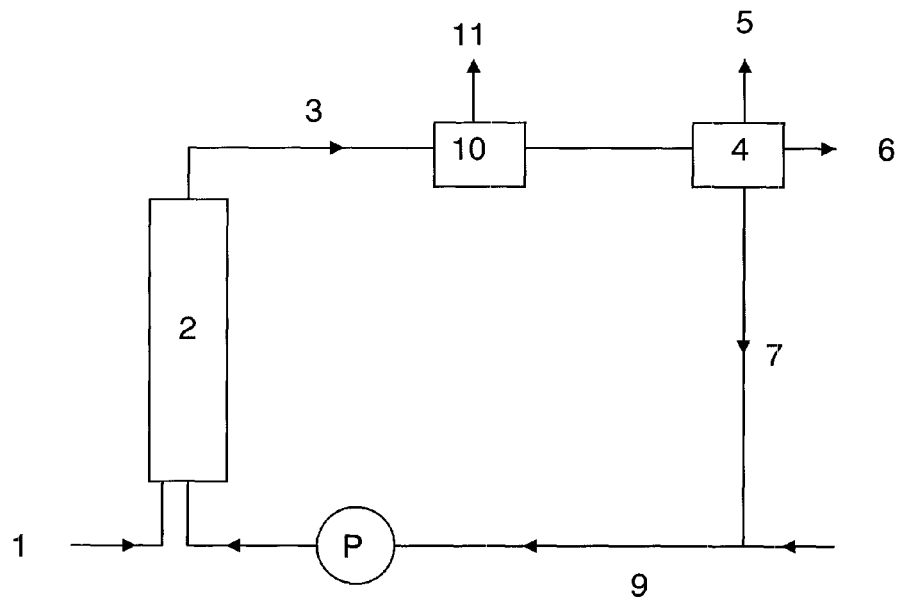
Figure 4:
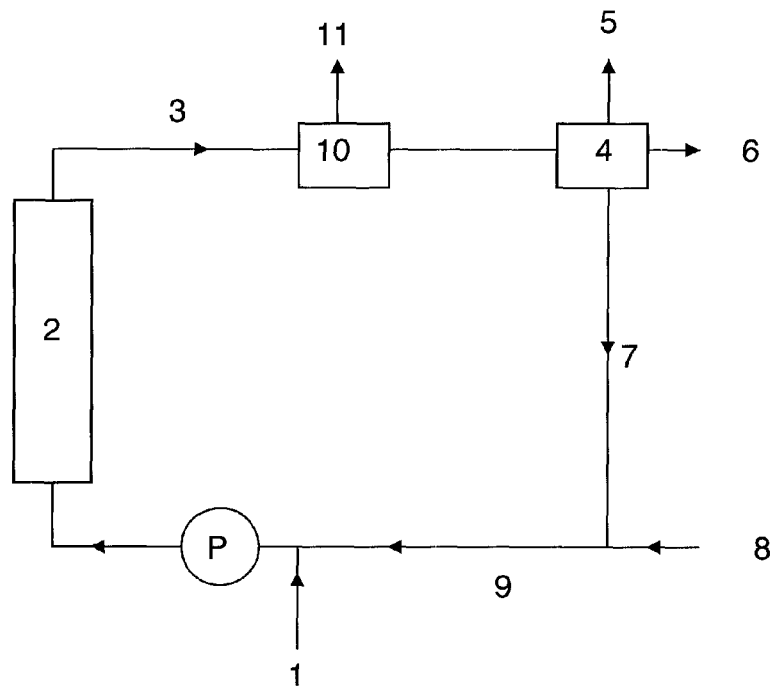

The process variant according to FIG. 3 differs from the embodiment according to FIG. 1 in that the reaction mixture (3), before the phase separation in the vessel (4), is subjected to a brief distillation. The process variant according to FIG. 4 likewise differs from the process variant according to FIG. 2.

EXAMPLES

The examples which follow are intended to illustrate the invention.

Test Apparatus/Test Evaluation

The aldol condensation of $C_5$-aldehydes by the process according to the invention was effected in a test plant which corresponded schematically to the process variant shown in FIG. 1.

The continuous catalyst phase 7 and 8 (sodium hydroxide solution) is circulated with a centrifugal pump P. The $C_5$-aldehyde (n-pentanal) or the $C_5$-aldehyde mixture (n-pentanal/2-methylbutanal) was added to the aqueous catalyst phase through line 1. The aldehyde can also be fed in upstream of the pump, as shown in FIG. 2. The multiphase mixture composed of aqueous catalyst phase and organic aldehyde phase obtained in this way was converted in a stainless steel tubular reactor 2.

The liquid stream (product and catalyst phase) 3 obtained downstream of the reactor was passed into a phase separation vessel 4. The aqueous catalyst phase (lower phase) was removed here and fed back to the circulation system via line 7. The organic phase (upper phase) comprising the reaction product, which runs over a weir in the phase vessel, can be withdrawn via line 5. The water of reaction formed can be discharged continuously via line 6. In order to compensate for the losses of sodium hydroxide solution resulting from discharge of the water of reaction, fresh 10% sodium hydroxide solution is metered in continuously via line 8 with a pH-regulated pump.

The metered addition of the fresh sodium hydroxide solution ensured that it was possible to keep the pH of the aqueous catalyst phase of 12.70±0.10 constant during the tests.

The heat of reaction was removed by means of the heat exchanger outside the reactor (not shown in FIG. 1).

For the performance of a comparative noninventive aldol condensation of aliphatic $C_5$-aldehydes, as described in Example I, a stirred reactor was used instead of a tubular reactor filled with static mixers.

Tables 1 to 5 appended to Examples 1 to 5 describe, in the upper region of the tables, the reaction conditions of the $C_5$-aldehyde condensation. In the lower region of the table for each example, the product composition is likewise listed in percent by mass of the GC analysis. For a better overview, no distinction is made between the isomers of the individual $C_{10}$-aldehydes or $C_{10}$-hydroxyalkanals (aldols). These values are combined as "2-propylheptenal" and "$C_{10}$-aldol" respectively. Likewise combined as "high boilers" are the by-products of the aldolization, such as trimers and tetramers, which have originated from the aldol reaction (addition and condensation) of three or four $C_5$-aldehydes.

The substance data and the equations and correlations detailed above were used to calculate the Sauter diameter and the energy input for the individual tests. These two parameters are likewise shown in the tables. The values for the density and the surface tension can be found in the specialist literature; in the present case, the density is about $1000 \, Kg/m^3$ and the surface tension is about $40 \cdot 10^{-3}$ N/m.

Example 1

Comparative Example

Preparation of 2-Propylheptenal from N-Pentanal in a Stirred Reactor:

2-Propylheptenal was prepared by condensation of n-pentanal in a stirred reactor in the form of an extraction column (volume 2.1 liters) with 10 mixing chambers which were equipped with 4-blade stirrers (diameter 68.1 mm) mounted on a stirrer axis. The continuous catalyst phase (2% sodium hydroxide solution) was circulated by means of a circulation pump. The n-valeraldehyde reactant was withdrawn from a 100 l vat (reactant reservoir) and pumped continuously into the NaOH circulation system through a thin capillary upstream of the reactor inlet. The mixture of product phase and aqueous catalyst phase was fed to a phase separation vessel downstream of the reactor. In the phase separation vessel, the organic product phase was removed from the catalyst phase. After the removal of the product phase, the aqueous phase was sent to the NaOH circulation system.

The catalyst circulation (2.0% aqueous NaOH, pH 12.85) was 80 l/h in all tests. The n-pentanal reactant was fed into the NaOH circulation system with a throughput of 8 l/h, corresponding to a phase ratio (PV) of organic phase to aqueous phase of 1 to 10. The reactant contained, as well as 98.3% by mass of n-pentanal, 1.7% by mass of secondary components including 0.2% by mass of $C_{10}$-aldols and 0.3% by mass of high boilers.

Table 1 shows the results of the aldolization of n-pentanal at 130° C. and pressure 4 bar at different stirrer speed (unit: revolutions per minute/rpm). In continuous operation after a test time of 3 hours, the following results were obtained in the steady state:

TABLE 1

| | I | II | III |
|---|---|---|---|
| Reaction conditions | | | |
| Stirrer speed (rpm) | 500 | 1000 | 2000 |
| Temperature (° C.) | 130 | 130 | 130 |
| PV (l of reactant/l of cat. phase) | 1 to 10 | 1 to 10 | 1 to 10 |
| Product composition | | | |
| n-Pentanal (% by mass) | 9.82 | 5.05 | 5.42 |
| 2-Propylheptenal (% by mass) | 86.25 | 92.14 | 92.25 |
| C10-Aldols (% by mass) | 0.08 | 0 | 0 |
| n-Pentanal conversion (%) | 90 | 94.8 | 94.5 |
| Sauter diameter (mm) | 0.13 | 0.057 | 0.025 |
| Energy input (W/m$^3$) | 3806 | 30675 | 245501 |

As can be inferred from Table 1, high stirrer speeds greater than 500 rpm are required for the achievement of high 2-propylheptenal contents of >92% by mass in the product output. Higher stirrer speeds apparently improve the mixing of the disperse organic phase with the aqueous phases. At stirrer speeds of 1000 rpm and higher, no influence of the stirrer speed on the achievable conversion of n-pentanal is found. The Sauter diameters calculated from the correlations for the stirred reactor are in the range from 0.025 to 0.13 mm depending on the stirrer speed.

Example 2

This example describes the process according to the invention for the aldol condensation of n-pentanal (n-valeraldehyde) to 2-propylheptenal (1+1 product), and the co-aldolization of n-pentanal with 2-methylbutanal to give the cross-product (1+2 product) 2-propyl-4-methylhexenal.

The reactor used was a DN15 tube (internal diameter 17.3 mm) of length 3 m with a total volume of 6.8 l. About 50% of the total volume of the tubular reactor was filled with static mixers with a hydraulic diameter of 2 mm and a relative void volume of 0.80. The mixing elements are formed from serrated lamellae which form open, crossing channels. The individual mixing elements at a distance of one mixing length were arranged offset by 90° from one another in the tubular reactor. The use of the static mixers was intended to balance out the inhomogeneities of the reaction mixture over the entire tube cross section.

The reactant for the tests was a $C_5$-aldehyde mixture consisting of 94.4% by mass of n-pentanal and 5.0% by mass of 2-methylbutanal, and also 0.6% by mass of secondary components including 0.1% by mass of high boilers.

At a circulation of the catalyst phase (2.1% aqueous sodium hydroxide solution, pH 12.98) of 80 l/h, just upstream of the inlet into the reactor filled with static mixers according to FIG. 1, reactant was introduced with a throughput of 2 l/h at three different temperatures of 110° C., 120° C. and 130° C.

Under the selected reaction conditions, a pressure drop $\Delta p$ of 0.049 bar was determined over the reactor length. The substance data for the biphasic system of n-pentanal and aqueous 2% sodium hydroxide solution was used, employing the equations detailed above, to calculate a mean droplet diameter (Sauter diameter $d_S$) of the disperse organic phase of about 0.91 mm.

The results recorded in Table 2 were achieved after 3 hours in the steady state:

TABLE 2

| | I | II | III |
|---|---|---|---|
| Reaction conditions | | | |
| Temperature (° C.) | 110 | 120 | 130 |
| PV (l of reactant/l of cat. phase) | 1 to 40 | 1 to 40 | 1 to 40 |
| Product composition | | | |
| n-Pentanal (% by mass) | 19.22 | 11.46 | 6.03 |
| 2-Methylbutanal (% by mass) | 3.48 | 2.56 | 2.79 |
| 2-Propylheptenal (% by mass) | 73.21 | 81.4 | 86.26 |
| 2-Propyl-4-methylhexenal | 3.6 | 3.63 | 4.09 |
| C10-Aldols (% by mass) | 0.01 | 0 | 0 |
| High boilers/residue (% by mass) | 0.48 | 0.95 | 0.84 |
| n-Pentanal conversion (%) | 79.6 | 87.8 | 93.6 |
| Sauter diameter (mm) | 0.91 | 0.91 | 0.91 |
| Energy input (W/m$^3$) | 315 | 315 | 315 |

As can be inferred from Table 2, the content of the 2-propylheptenal product of value increases significantly from 73.21 to 86.26% by mass with the temperature rise from 110 to 130° C. In contrast, the temperature dependence of the second product of value, 2-propyl-4-methylhexenal (cross-product of the n-pentanal/2-methylbutanal aldol condensation), is significantly lower.

Compared to aldolization tests in the stirred reactor (see Example 1 Columns II and III of Table 1), comparable conversions are achieved in the case of use of static mixers (see Column III of Table 2), the energy input being 97 to 780 times lower.

Example 3

This example describes the process according to the invention for the aldol condensation of n-pentanal (n-valeraldehyde) to 2-propylheptenal (1+1 product) and the co-aldolization of n-pentanal with 2-methylbutanal to give the cross-product (1+2 product), 2-propyl-4-methylhexenal. In contrast to Example 2, the reactor used was a DN15 tube (internal diameter 17.3 mm) not of length 3 m but of length 4 m, with a total volume of 9.1 l. In this example too, about 50% of the total volume of the tubular reactor was filled with static mixers with a hydraulic diameter of 2 mm and a relative void volume of 0.80.

The reactant used for the tests was a $C_5$-aldehyde mixture consisting of 93.7% by mass of n-pentanal and 5.2% by mass of 2-methylbutanal, and also 1.1% by mass of secondary components including 0.8% by mass of $C_{10}$-aldols and 0.1% by mass of high boilers. At 130° C. and a pressure of 4 bar, at a constant circulation of the NaOH phase (2.1% aqueous sodium hydroxide solution) of 80 l/h, the throughput of the reactant was in the range from 2.2 l/h to 8.4 l/h. The $C_5$-aldehyde mixture was metered in just upstream of the inlet into the reactor filled with static mixers according to FIG. 1. In continuous operation, after a test time of 4 hours at the steady state, the following results were obtained:

TABLE 3

|  | I | II | III |
|---|---|---|---|
| Reaction conditions |  |  |  |
| Temperature (° C.) | 130 | 130 | 130 |
| Reactant C5-aldehydes (l/h) | 2.2 | 4.1 | 8.4 |
| PV (l of reactant/l of cat. phase) | 1 to 36 | 1 to 19.5 | 1 to 9.5 |
| Product composition |  |  |  |
| n-Pentanal (% by mass) | 3.72 | 5.04 | 11.09 |
| 2-Methylbutanal (% by mass) | 2.67 | 2.29 | 2.3 |
| 2-Propylheptenal (% by mass) | 88.51 | 87.59 | 81.2 |
| 2-Propyl-4-methylhexenal | 4.6 | 3.8 | 3.55 |
| C10-Aldols (% by mass) | 0 | 0.18 | 0.87 |
| High boilers/residue (% by mass) | 0.5 | 0.77 | 0.98 |
| n-Pentanal conversion (%) | 96 | 94.6 | 87.2 |
| Sauter diameter (mm) | 0.91 | 0.89 | 0.85 |
| Energy input (W/m$^3$) | 318 | 315 | 395 |

The increase in the reaction volume resulting from extension of the tubular reactor by one meter led, at the same reactor loading, compared to Example 2, to longer residence times and to a rise in the pressure drop from 0.049 to 0.066 bar.

As a result of the longer residence time owing to the extended tubular reactor, it was possible to enhance the n-pentanal conversion, with a reactant throughput of about 2 l/h, from 93.6% (see Table 2 Column III) to 96% (see Table 3 Column I).

As can be seen in Table 3 Column II, conversions of >94% were also achieved at an increased reactant throughput of 4.1 l/h. The present results show that the achievable n-pentanal conversions are influenced less by the phase ratio selected, and instead significantly more by the selected residence time of the organic phase in the reactor. At a reactant throughput of 8.4 l/h, the residence time is too short to achieve a higher n-pentanal conversion than 87.2%.

Example 4

This example describes the process according to the invention for the aldol condensation of n-pentanal (n-valeraldehyde) to 2-propylheptenal (1+1 product), and the co-aldolization of n-pentanal with 2-methylbutanal to give the cross-product (1+2 product), 2-propyl-4-methylhexenal. In contrast to Example 3, the total volume of the tubular reactor (DN15 tube (internal diameter 17.3 mm) with a volume of 9.1 l was filled completely with static mixers with a hydraulic diameter of 2 mm and a relative void volume of 0.80.

The reactant used was a $C_5$-aldehyde mixture consisting of 94.4% by mass of n-pentanal and 5.0% by mass of 2-methylbutanal, and also 0.6% by mass of secondary components including 0.2% by mass of $C_{10}$-aldols and 0.1% by mass of high boilers. The composition of the reactant was comparable to the composition of the $C_5$-aldehyde mixture used in Example 3.

At 130° C. and a pressure of 4 bar, at a constant circulation of the NaOH phase (2.1% aqueous sodium hydroxide solution) of 80 l/h, 4.1 l/h of reactant were metered into the catalyst circulation system upstream of the inlet into the reactor according to FIG. 1.

In continuous operation, after a test time of 4 hours in the steady state, the following results were obtained, which are shown in Table 4 Column I. Column II lists, for comparison, the results of the test from Example 3 in a tubular reactor whose total volume was 50% covered with static mixers.

TABLE 4

|  | I | II |
|---|---|---|
| Reaction conditions |  |  |
| Proportion by volume of the stat. mixers (%) | 100 | 50 |
| Temperature (° C.) | 130 | 130 |
| Reactant C5-aldehydes (l/h) | 4.1 | 4.1 |
| PV (l of reactant/l of cat. phase) | 1 to 19.5 | 1 to 19.5 |
| Product composition |  |  |
| n-Pentanal (% by mass) | 6.87 | 5.04 |
| 2-Methylbutanal (% by mass) | 2.32 | 2.29 |
| 2-Propylheptenal (% by mass) | 86.72 | 87.59 |
| 2-Propyl-4-methylhexenal | 3.35 | 3.8 |
| $C_{10}$-Aldols (% by mass) | 0.05 | 0.18 |
| High boilers/residue (% by mass) | 0.68 | 0.77 |
| n-Pentanal conversion (%) | 92.7 | 94.6 |
| Sauter diameter (mm) | 0.89 | 0.89 |
| Energy input (W/m3) | 339 | 339 |

Complete coverage of the tubular reactor with static mixers led, as shown in Table 4 in Column I, compared to 50% filling by the process according to the invention (Table, Column 3), not to an increase but to a decline in the n-pentanal conversion.

Example 5

This example describes the process according to the invention for the aldol condensation of n-pentanal (n-valeraldehyde) to 2-propylheptenal (1+1 product), and the co-aldolization of n-pentanal with 2-methylbutanal to give the cross-product (1+2 product), 2-propyl-4-methylhexenal. The reactor used was, as in Example 3, a DN15 tube (internal diameter 17.3 mm) of length 4 m with a total volume of 9.1 l. About 50% of the total volume of the tubular reactor was filled with static mixers. In contrast to Example 3, the $C_5$-aldehyde mixture reactant was not fed in upstream of the reactor, but instead into the NaOH circulation system upstream of the circulation pump according to FIG. 2.

The reactant used was a $C_5$-aldehyde mixture consisting of 94.4% by mass of n-pentanal and 5.0% by mass of 2-methylbutanal, and also 0.6% by mass of secondary components including 0.2% by mass of $C_{10}$-aldols and 0.1% by mass of high boilers. The composition of the reactant was comparable to the composition of the $C_5$-aldehyde mixture used in Example 3. At 130° C. and a pressure of 4 bar, at a circulation of the aqueous NaOH phase (about 2% aqueous sodium hydroxide solution) of 80 l/h and 40 l/h, 4.1 l/h of reactant were metered into the catalyst circulation system upstream of the circulation pump.

Lowering the circulation from 80 to 40 l/h alters the flow hydrodynamics and the mean droplet diameter (Sauter diameter) of the disperse phase. The Sauter diameter calculated on the basis of the aforementioned correlations rises from 0.91 mm to 1.54 mm.

In continuous operation, after a test time of 4 hours in the steady state, the following results were obtained in this method, which are shown by Table 5 in Columns I and II. Column III lists, for comparison, the results of the test from Example 3 with metered addition of reactant upstream of the reactor.

TABLE 5

|  | I | II | III |
|---|---|---|---|
| Reaction conditions |  |  |  |
| Site of metered addition of reactant | Upstream of pump | Upstream of pump | Upstream of reactor |
| Temperature (° C.) | 130 | 130 | 130 |
| NaOH circulation (l/h) | 40 | 80 | 80 |
| Reactant C5-aldehydes (l/h) | 4.1 | 4.1 | 4.1 |
| PV (l of reactant/l of cat. phase) | 1 to 9.7 | 1 to 19.5 | 1 to 19.5 |
| Product composition |  |  |  |
| n-Pentanal (% by mass) | 4.53 | 4.77 | 5.04 |
| 2-Methylbutanal (% by mass) | 2.33 | 2.31 | 2.29 |
| 2-Propylheptenal (% by mass) | 88.1 | 88.14 | 87.59 |
| 2-Propyl-4-methylhexenal | 3.91 | 3.84 | 3.8 |
| C10-Aldols (% by mass) | 0.11 | 0.17 | 0.18 |
| High boilers/residue (% by mass) | 1.01 | 0.78 | 0.77 |
| n-Pentanal conversion (%) | 95.2 | 94.9 | 94.6 |
| Sauter diameter (mm) | 1.54 | 0.91 | 0.91 |

The metered addition of reactant according to FIG. 2 led, as shown in Table 5, to an improvement in the conversions. In the present process according to the invention, it is possible to use both variants of reactant metering detailed in the aldol condensation of $C_5$-aldehydes to $\alpha,\beta$-unsaturated $C_{10}$-aldehydes.

Example 6

Phase Separation of the Product of the $C_5$-aldehyde Aldolization

This example describes the preferred phase separation of the reaction output of the aldol condensation of n-pentanal to 2-propylheptenal, and the co-aldolization of n-pentanal with 2-methylbutanal to give 2-propyl-4-methylhexenal at temperatures in the range from 70 to 120° C.

For the performance of the tests, for phase separation, prior to the continuous aldolization tests, the aqueous phase and the organic product of value phase were withdrawn from the reactor. For the phase separation tests, a heated 2 l jacketed glass reactor was used, which was equipped with a stirrer. The phase separation temperature in the range from 40 to 110° C. was regulated by means of a thermostat. First, the two phases were transferred into the reactor at a phase ratio (org. phase/ $H_2O$ phase) of 1 to 10 and the pressure was set to 3.5 bar, i.e. to the same value as in the aldolization plant. Once the two phases had been brought to the test temperature with slow stirring, the stirrer was started at 500 revolutions per minute (rpm) for 2 minutes. The intensive stirring ensured that the two phases were mixed well with one another. After 3 minutes had expired, the stirrer was stopped and the time for the phase separation was determined.

Firstly recorded was the separation time required by the two phases to separate completely from one another with a clearly visible phase interface. Secondly determined was the time needed by the phases to become clear again. A clear product of value phase substantially rules out the presence of finely distributed disperse water droplets in the organic phase. At each temperature setting, the separation test was carried out five times and the mean was formed from the results obtained. After the separation tests, the organic phases withdrawn were analysed by GC and wet-chemical means.

The wet-chemical methods were used to determine the water contents (Karl-Fischer) and the sodium salt contents (by titrimetric means) in the organic phases.

In the aqueous phases, as well as the NaOH and sodium salt contents, the total carbon content was additionally determined.

The organic phase used for the separation tests contained, after the analysis, about 0.79% by mass of homogeneously dissolved water and no traces of sodium hydroxide solution. The aqueous NaOH phase contained, as well as 2.02% by mass of NaOH, about 0.30% by mass of sodium salt and 1.1% by mass of total carbon. The results of the examinations of phase separation are compiled in Table 6.

TABLE 6

| Phase separation |  |  |  |  |
|---|---|---|---|---|
| Temperature (° C.) | 50 | 70 | 90 | 110 |
| Time for phase separation (s) | 37 | 25 | 21 | 17 |
| Time for phase clarification (min) | 25 | 11 | 8 | 4 |
| Analysis/organic phase |  |  |  |  |
| NaOH content (% by mass) | 0 | 0 | 0 | 0 |
| Water (% by mass) | 1.02 | 0.95 | 0.93 | 1.27 |
| Analysis/aqueous phase |  |  |  |  |
| NaOH content (% by mass) | 2.01 | 2.03 | 2.06 | 2.02 |
| Sodium salt (% by mass) | 0.33 | 0.34 | 0.31 | 0.34 |
| Total carbon (% by mass) | 1.1 | 1.1 | 1.1 | 1.1 |

The sodium salt in Table 6 is principally sodium pentoxide.

With rising phase separation temperature within the range from 50 to 110° C., the separation of the organic phase from the aqueous phase is improved. This applies both to the actual phase separation (formation of the phase interface) and to the clarification of the organic phase (clear phase without turbidity).

The time for the formation of the phase interfaces is comparatively short; at 17 to 37 seconds, it is within the range of seconds. The phases clarify much more slowly, in the course of which the residual heterogeneous water droplets, inter alia, are removed.

As can be inferred from Table 6, the time for the phase clarification can be shortened significantly by increasing the temperature from 50 to 70° C. and higher.

According to all of the above, a particularly preferred embodiment of the invention can be specified as follows:

A continuous process for preparing $\alpha,\beta$-unsaturated $C_{10}$-aldehydes from aliphatic $C_5$-aldehydes, which comprises the following steps:

a) aldol condensation of aliphatic $C_5$-aldehydes to give $\alpha,\beta$-unsaturated $C_{10}$-aldehydes in the presence of an aqueous base in a tubular reactor, which has at least one mixer module which disperses the reactant or reactant/product mixture in the process liquor as droplets with an average Sauter diameter in the range from 0.2 to 2 mm, b) phase separation of the reactor output from step a) into an aqueous catalyst phase and an organic product phase, c) separation of the organic phase from step b) into $\alpha,\beta$-unsaturated $C_{10}$-aldehydes, aliphatic $C_5$-aldehydes and by-products, d) recycling into the reactor of a portion of the aqueous phase from step b) after supplementation with fresh base and partial discharge of the water of reaction, the aqueous process liquor, at a pH in the range from 12.5 to 13.5, containing sodium hydroxide and sodium salts of carboxylic acids, and e) separation of the organic product phase from step b) from the aqueous catalyst phase at temperatures in the range from 70 to 120° C.

The invention claimed is:

1. A process for continuously preparing an α,β-unsaturated $C_{10}$-aldehyde from an aliphatic $C_5$-aldehyde, comprising:
   a) condensing by aldol condensation an aliphatic $C_5$-aldehyde to give an α,β-unsaturated $C_{10}$-aldehyde in the presence of an aqueous base in a tubular reactor;
   b) separating the output from the tubular reactor into an aqueous catalyst phase and an organic product phase;
   c) separating the organic product phase into α,β-unsaturated $C_{10}$-aldehyde, aliphatic $C_5$-aldehyde and by-products;
   d) discharging a portion of the aqueous catalyst phase to remove the water of reaction and supplementation with fresh base and subsequent recycling into the tubular reactor;
   wherein the aliphatic $C_5$-aldehyde and/or the α,β-unsaturated $C_{10}$-aldehyde are dispersed as droplets in the aqueous base; wherein the average Sauter diameter of the droplets is in the range from 0.2 mm to 1.54 mm.

2. The process according to claim 1, wherein the pH of the aqueous base is in the range from 12.5 to 13.5, and the aqueous base comprises sodium hydroxide and sodium salts of carboxylic acids.

3. The process according to claim 1, wherein the phase separation of the output from the tubular reactor into the aqueous catalyst phase and the organic product phase is effected at temperatures in the range from 70° C. to 120° C.

4. The process according to claim 1, wherein the reaction temperature in the tubular reactor is in the range from 120° C. to 140° C.

5. The process according to claim 1, wherein the ratio of the mass of aqueous base to the mass of the aliphatic $C_5$-aldehyde at the inlet of the tubular reactor is in the range from 5 to 20.

6. The process according to claim 1, wherein the average superficial velocity of the mixture of aqueous base and aliphatic $C_5$-aldehyde is in the range from 0.5 to 4 m/s.

7. The process according to claim 1, wherein the average residence time of the starting mixture in the tubular reactor is 40 to 360 seconds.

8. The process according to claim 1, wherein a $C_5$-aldehyde mixture with an n-pentanal content of at least 90% by mass is used.

9. The process according to claim 1, wherein the aliphatic $C_5$-aldehyde and/or the α,β-unsaturated $C_{10}$-aldehyde are dispersed in the aqueous base within the tubular reactor.

10. The process according to claim 9, wherein the aliphatic $C_5$-aldehyde and/or the α,β-unsaturated $C_{10}$-aldehyde are dispersed in the aqueous base within the tubular reactor with the aid of at least one mixing module installed in the tubular reactor.

11. The process according to claim 10, wherein the aliphatic $C_5$-aldehyde and/or the α,β-unsaturated $C_{10}$-aldehyde are dispersed in the aqueous base within the tubular reactor with the aid of at least two mixing modules installed in the tubular reactor.

12. The process according to claim 10, wherein the proportion of the volume of the mixing module(s) in the total volume of the reactor is 20 to 80%.

13. The process according to claim 12, wherein the distance between two adjacent mixing modules is 0.2 to 5 times the length of the mixing modules.

14. The process according to claim 11, wherein the distance between two adjacent mixing modules decreases in flow direction.

15. The process according to claim 1, wherein the loading factor is in the range from 0.2 to 0.8.

16. The process according to claim 1, wherein the average Sauter diameter of the droplets is in the range from 0.6 mm to 1.54 mm.

17. The process according to claim 1, wherein the average Sauter diameter of the droplets is in the range from 0.6 mm to 1.3 mm.

18. The process according to claim 1, wherein the average residence time of the starting mixture in the tubular reactor is 60 to 180 seconds.

* * * * *